United States Patent [19]
Golser et al.

[11] Patent Number: 5,735,867
[45] Date of Patent: Apr. 7, 1998

[54] WORKING CANNULA FOR ARTHROSCOPY

[76] Inventors: Karl Golser; Gernot Sperner, both of Anichstrasse 35, A-6020 Innsbruck, Austria

[21] Appl. No.: 681,854

[22] Filed: Jul. 29, 1996

[30] Foreign Application Priority Data

Aug. 23, 1995 [AT] Austria ................... GM 454/95

[51] Int. Cl.⁶ ............................................. A61B 17/34
[52] U.S. Cl. ..................................... 606/185; 604/164
[58] Field of Search ............................. 604/164, 265; 606/185, 167, 169, 108, 184

[56] References Cited

U.S. PATENT DOCUMENTS

| | | | |
|---|---|---|---|
| 4,573,448 | 3/1986 | Kambin . | |
| 5,258,003 | 11/1993 | Ciaglia et al. | 606/185 |
| 5,556,411 | 9/1996 | Taoda et al. | 606/185 |
| 5,591,190 | 1/1997 | Yoon | 606/185 |

FOREIGN PATENT DOCUMENTS

| | | |
|---|---|---|
| 0346469 | 12/1989 | European Pat. Off. . |
| 1521465 | 11/1989 | U.S.S.R. . |
| 9325148 | 12/1993 | WIPO . |

*Primary Examiner*—Michael Buiz
*Assistant Examiner*—Kevin Troung
*Attorney, Agent, or Firm*—Lorusso & Loud

[57] ABSTRACT

A working cannula for arthroscopy, in particular of the shoulder and the knee, comprising a tube and a removable closure pin member (trocar) which is guided in the tube, wherein the tube has an external screwthread which is continued by a screwthread of the tip, which projects beyond the tube, of the closure pin member. The closure pin member has a central bore extending therethrough, for receiving a guide wire. The closure pin member locks on to the tube so that when the closure pin is rotated, the tube rotates to facilitate anchoring of the screwthread into a patient.

6 Claims, 2 Drawing Sheets

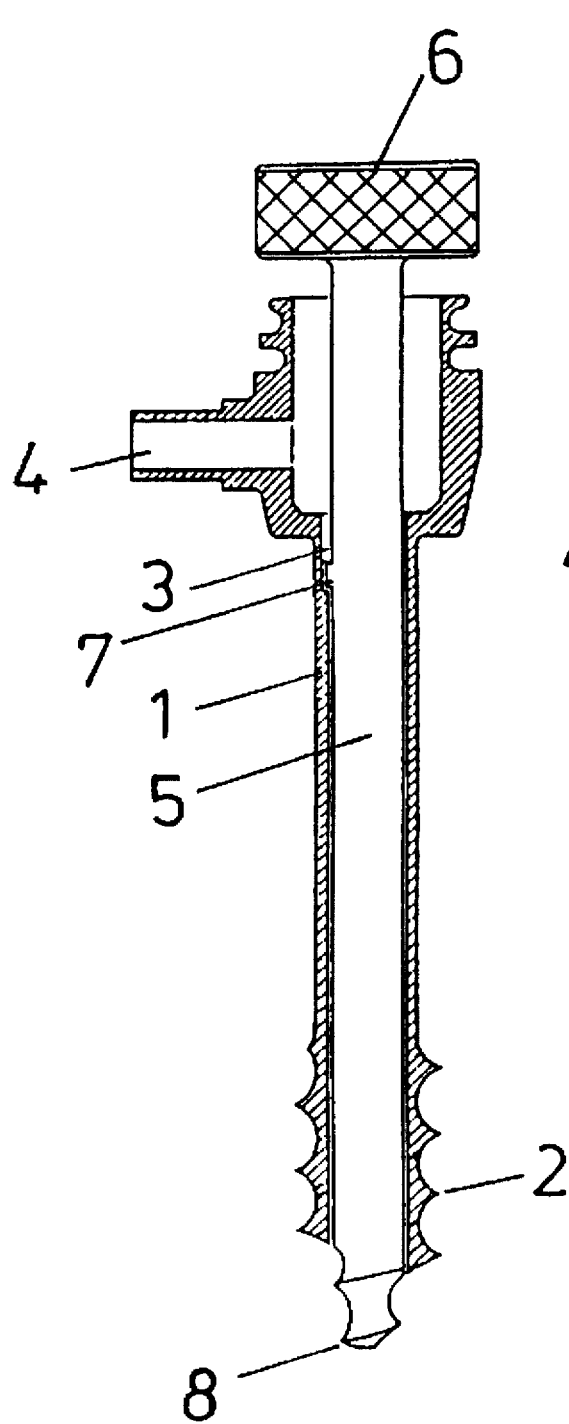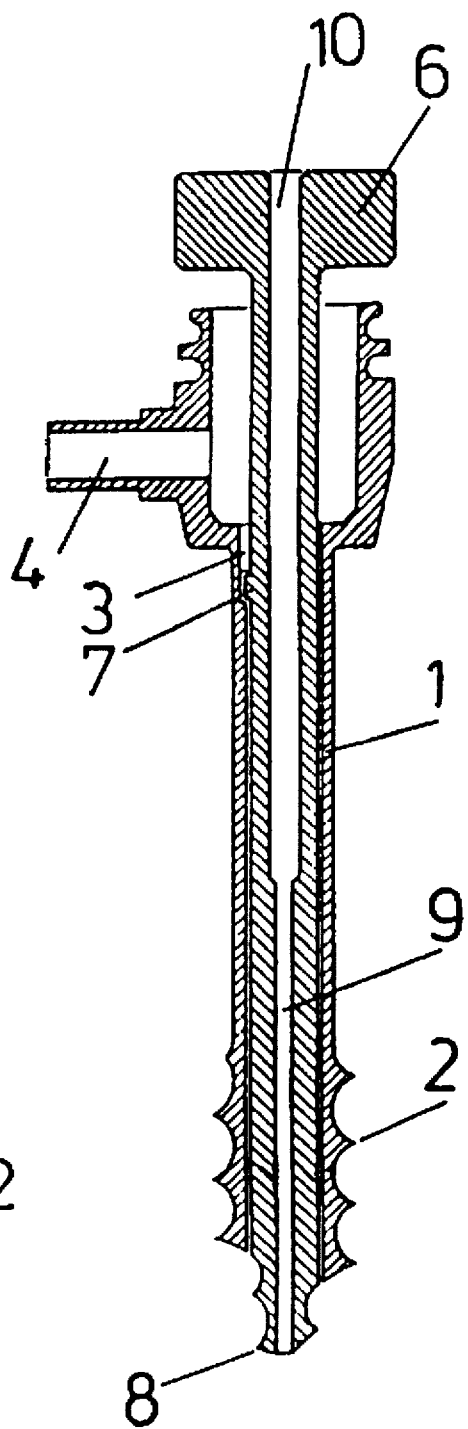

WORKING CANNULA FOR ARTHROSCOPY

BACKGROUND OF THE INVENTION

1. Field of the Invention

The field of this invention is a medical device, particularly, those used for arthroscopic procedures and a method for performing arthroscopic procedures.

2. Description of the Prior Art

In a known device which is marketed by Arthrex, the closure pin member is provided with a blunt front end as a point could result in injuries, in particular also of nerves, while a blunt pin member can be pressed through the muscle tissue.

On the other hand SU-A1 15 21 465 already discloses a device comprising a trocar sleeve and a trocar, wherein the trocar sleeve has in the distal end region an external screwthread which is continued by the screwthread of the trocar tip.

In the first-mentioned design the device has a relatively low capability of proper targeting. On the other hand, in the case of a working cannula which is provided with a screwthread, a critical consideration is immediately finding the correct position in the joint as screwing in the sharp-edged device a plurality of times is something that is absolutely to be avoided.

SUMMARY OF THE INVENTION

The invention concerns a working cannula for arthroscopy, in particular of the shoulder and the knee, comprising a tube and a removable closure pin member (trocar) which is guided in the tube, wherein the tube has an external screwthread which is continued by a screwthread of the tip, which projects beyond the tube, of the closure pin member. In accordance with the invention, the tube and trocar are locked together so that when the trocar is turned the entire device turns.

The invention guarantees properly targeted insertion of the working cannula by virtue of the closure pin member having a central bore extending therethrough, for receiving a guide wire.

In itself it seems paradoxical for the closure pin member (trocar), the purpose of which is to close off the trocar sleeve, itself in turn to be in the form of a sleeve. The central bore in the closure pin member, which is provided in accordance with the invention, is however securely closed by the guide wire during insertion of the working cannula.

BRIEF DESCRIPTION OF THE DRAWING

Details of the invention are described hereinafter with reference to the drawings in which:

FIG. 3 is a view in partial section through FIG. 2, and

FIG. 4 is a complete longitudinal section of the device shown in FIG. 2 and FIG. 3 respectively.

DESCRIPTION OF THE PREFERRED EMBODIMENTS

Figure 1:
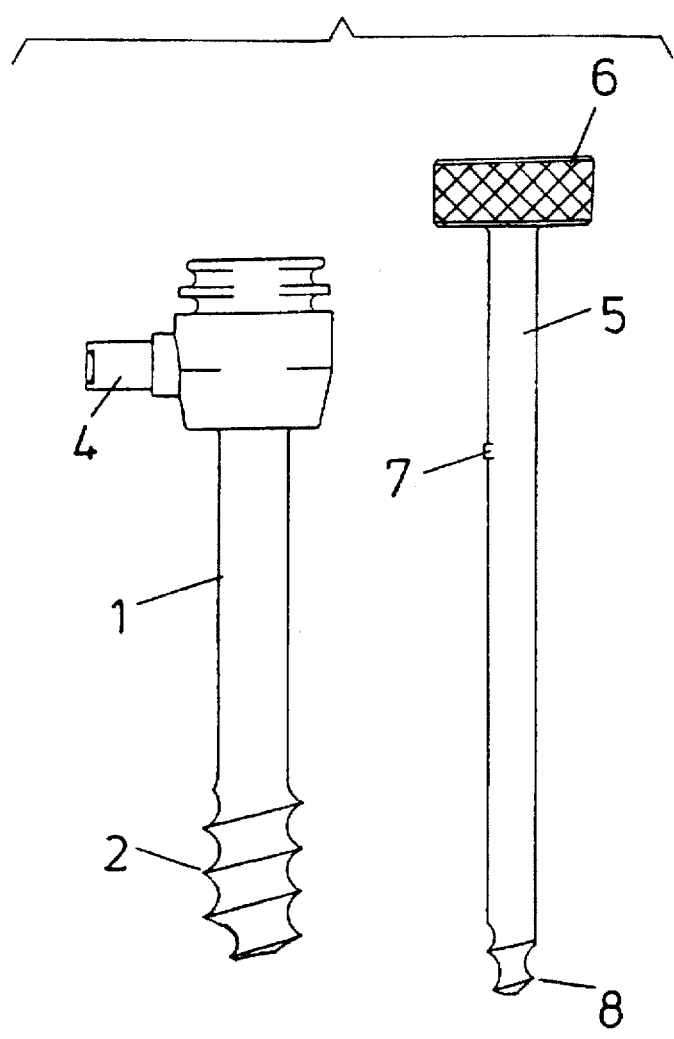
FIG. 1 is a side view showing the two parts of an embodiment, separately.
Figure 2:
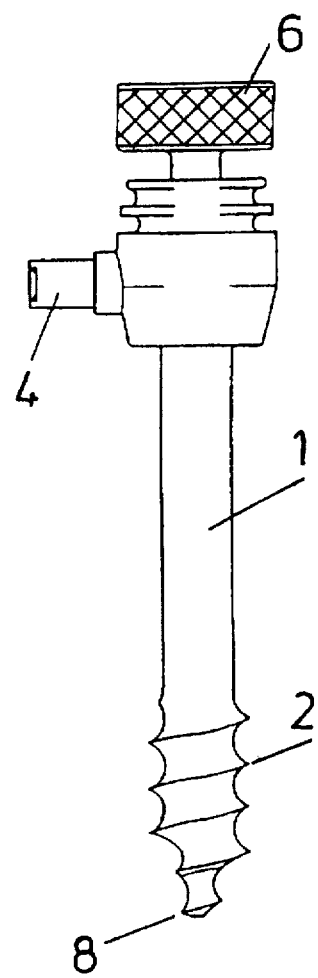
FIG. 2 shows the device of FIG. 1 in the assembled condition.

An essential part of a working cannula for arthroscopy is a tube 1 which is provided in the present case with a sharp-edged screwthread 2. Disposed at the outer end is a connecting portion 4 through which for example a fluid can be pressed in.

When the tube 1 is inserted into a joint, in particular into the shoulder joint, the tube 1 is filled by a closure pin member 5 whose tip which is provided with a screwthread 8 projects through the tube 1 and continues the screwthread thereof in such a way that the diameter decreases quickly towards the tip. A projection 7 on the outside of the closure pin member 5 engages into an enlargement 3 in the tube when the closure pin member 5 is entirely inserted into the tube 1. In that way, as can be seen from FIG. 3, the tube 1 can be screwed in by means of the rotary grip 6 which is arranged on the closure pin member 5.

An essential aspect of the invention is the central bore 9 in the closure pin member 5, which goes into an enlargement 10 in the direction of the rotary grip 6.

The diameter of the bore 9 is about 1 ram, thereby affording a secure hold for a guide wire. In particular a pointed wire of spring steel, which is known as 'Kirschner' wire, falls to be considered as a secure guide wire, that wire being elastically deformable and affording a high breaking strength.

In an operation firstly an arthroscope is inserted and then in the area of view thereof the guide wire is put in to the desired location. With the target location secured by the guide wire, the device consisting of the tube 1 and the closure pin member 5 (trocar sleeve and trocar) is now screwed in by way of the guide wire, with the rotary grip 6 being rotated. The guide wire and the closure pin member 5 are then pulled out, in which case the screwthread 2 holds the tube 1 in its position so that now the desired manipulation operations can be effected through the tube 1.

We claim:

1. An arthroscopic device for performing arthroscopic procedures comprising a cannula and a trocar, said cannula defining a central bore adapted to receive said trocar, said trocar defining a central bore for receiving a guidewire, said cannula having screw threads at its distal end, said trocar having screw threads at its distal end, said cannula and said trocar being designed so that when said trocar is inserted to its fullest extent in the central bore of said cannula, the distal ends of said trocar and said cannula form a continuous thread pattern located on the distal end of said arthroscopic device.

2. The device as set forth in claim 1 wherein the cannula includes an inlet for fluids through its sidewall in fluid communication with the central bore in the cannula.

3. An arthroscopic device for performing arthroscopic procedures comprising a cannula and a trocar, said cannula defining a central bore adapted to receive said trocar, said trocar defining a central bore for receiving a guidewire, said trocar including a protrusion which mates with a recess included in said cannula such that when said trocar is fully inserted in said cannula, said trocar is locked in position inside said cannula and said cannula rotates when said trocar is turned.

4. The device as set forth in claim 3 wherein the cannula includes an inlet for fluids through its sidewall in fluid communication with the central bore in the cannula.

5. In a device for performing arthroscopic procedures of the type which includes a cannula and a trocar, wherein the improvement comprises screwthreads on the cannula which mate with screwthreads on the trocar when the trocar is inserted in the cannula and being further characterized in that the cannula and the trocar can be locked together so that when the trocar is rotated, the cannula also rotates to facilitate the screwthreads securing the cannula to a patient.

6. A method for performing an arthroscopic procedure, comprising the following steps;

1) inserting a guidewire into the desired location in a patient,
2) providing a cannula surrounding a trocar with screw threads on the distal ends of both the cannula and the trocar, said trocar having a center bore to accommodate the guidewire,
3) locking the trocar and the cannula to form an arthroscopic device so that when the trocar is rotated the cannula also rotates,
4) positioning the guidewire through the trocar,
5) securing the device to the patient by rotating the trocar, and
6) removing said guidewire and said trocar to leave the cannula screwed in place to facilitate the arthroscopic procedure.

* * * * *